United States Patent
Garg et al.

(10) Patent No.: US 6,283,997 B1
(45) Date of Patent: Sep. 4, 2001

(54) CONTROLLED ARCHITECTURE CERAMIC COMPOSITES BY STEREOLITHOGRAPHY

(75) Inventors: Rajeev Garg, Northwales, PA (US); Robert K. Prud'Homme, Princeton Jnct, NJ (US); Ilhan A. Aksay, Princeton, NJ (US); Victor F. Janas, Monroe Township, NJ (US); Kevor S. TenHuisen, Neshanic Station, NJ (US); Shawn T. Huxel, Lakehurst, NJ (US)

(73) Assignees: The Trustees of Princeton University, Princeton; Ethicon, Inc., New Brunswick, both of NJ (US)

( * ) Notice: Subject to any disclaimer, the term of this patent is extended or adjusted under 35 U.S.C. 154(b) by 0 days.

(21) Appl. No.: 09/191,606

(22) Filed: Nov. 13, 1998

(51) Int. Cl.$^7$ ........................................................ A61F 2/28
(52) U.S. Cl. ................... 623/16.11; 623/901; 623/23.51; 623/23.56
(58) Field of Search .................... 623/16, 23.51, 623/901, 23.56, 16.11; 430/269

(56) References Cited

U.S. PATENT DOCUMENTS

| | | | | |
|---|---|---|---|---|
| 4,575,330 | * | 3/1986 | Hull .................................. | 425/174.4 |
| 4,777,153 | * | 10/1988 | Sonupariak et al. .................... | 501/82 |
| 4,842,603 | * | 6/1989 | Draenart .................................. | 623/16 |
| 4,976,738 | * | 12/1990 | Frey et al. .............................. | 623/16 |
| 5,370,692 | * | 12/1994 | Fink et al. .............................. | 623/16 |
| 5,496,682 | * | 3/1996 | Quadir et al. ......................... | 430/269 |
| 5,847,046 | * | 12/1998 | Jiang et al. ............................ | 524/42 |

* cited by examiner

Primary Examiner—Corrine McDermott
Assistant Examiner—Choon P. Koh
(74) Attorney, Agent, or Firm—Wolff & Samson

(57) ABSTRACT

A process for producing a ceramic composite having a porous network. The process includes providing a photocurable ceramic dispersion. The dispersion consists of a photocurable polymer and a ceramic composition. The surface of the dispersion is scanned with a laser to cure the photocurable polymer to produce a photocured polymer/ceramic composition. The photocured composition useful as a polymer/ceramic composite, or the polymer phase can be removed by heating to a first temperature that is sufficient to burn out the photocured polymer. It is then heated to a second temperature that is higher than the first temperature and is sufficient to sinter the ceramic composition to produce a purely ceramic composition having a porous network.

Preferably and more specifically, the process uses a stereolithographic technique for laser scanning. The process can form a high quality orthopedic implant that dimensionally matches the bone structure of a patient. The technique relies upon laser photocuring a dense colloidal dispersion into a desired complex three-dimensional shape. The shape is obtained from a CAT scan file of a bone and is rendered into a CAD file that is readable by the stereolithography instrument. Or the shape is obtained directly from a CAD file that is readable by the stereolithography instrument.

20 Claims, 2 Drawing Sheets

CONTROLLED ARCHITECTURE CERAMIC COMPOSITES BY STEREOLITHOGRAPHY

BACKGROUND OF THE INVENTION

1. Field of the Invention

This invention relates to ceramic and polymer/ceramic composites having a porous network wherein the macroshape of the composite, microarchitecture of the network, porosity and the pore sizes in the network can be simultaneously and precisely controlled or designed. This invention further relates to methods for producing such composites by stereolithography and the varied uses thereof.

2. Related Art

Micro-architecture and pore size are extremely important for osteoconduction in ceramic bone grafts. All of our organs (such as liver, bone, and kidney) constitute a "Parenchyma," which is the physiologically active component, and the "Stroma," which is the framework that supports the organization of the parenchyma. In soft tissue, loss of parenchyma with maintenance of stroma allows a remarkable degree of regeneration and repair. Thus to design an implant for osteoconduction it is desirable to mimic the architecture of the interstitial or stromal bone. An idealized bone graft substitute would mimic osteon-evacuated bone and have an interconnected porous system of channels of similar dimension. Many in vivo studies have revealed the significance of the porous structure on the promotion of bone growth.

The fabrication of such osteon-evacuated complex architecture or controlled microarchitecture and controlled porosity ceramic and ceramic/polymer composite structures is difficult and has been the subject of many investigations. See, for example, Fabbri et al., *Biomaterials* 16 (1995) pp. 225 et seq; Liu, "Fabrication of Hydroxyapatite Ceramic with Controlled Porosity," *J. Mater. Res.Mater. Med.* 8 (1997) pp. 227–232; Arita et al., *J.Mater.Sci.Mater. Med.* 6 (1995) pp. 19; and Fabbri et al., "Granulates Based on Calcium Phosphates with Controlled Morphology and Porosity for Medical Applications," *Biomaterials* 6 (1994) pp.474–477.

Classical studies by Hulbert et al., "Potential of Ceramic Materials as Permanently Implantable Skeletal Prostheses," *J. Biomed. Mater. Res.* 4(1970) pp.433–456, as early as 1971established minimum pore size requirements of 100 microns for successful bone in-growth. Klein et al., "Macroporous Calcium Phosphate Bioceramics in Dog Femora: A Histological Study of Interface and Biodegradation," *Biomaterials* 10 (1989) pp.59–62, studied sintered HAp material containing pores of 150–250 microns in dog femurs. The volume fraction porosity and pore interconnectivity was not disclosed. Constantino, et al., "Hydroxyapatite Cement: I. Basic Chemistry and Histologic Properties," *Arch. Otolaryngol. Hecul. Neck Surg.* 117 (1991) pp. 379–384, studied HAp cement material that had a volume fraction porosity of 10% and 20%. The pore dimensions and connectivity were not reported. The ideal pore dimensions and the porosity of the interconnected porous system for osteo-conduction has still not been determined or achieved.

Currently, there is one product available with a porous infrastructure similar to that of bone. This structure is made by a process named "replaminform" which utilizes the skeletal structure of marine invertebrates, especially reef building corals, as a template to make porous structures. Roy et al., "Hydroxyapatite Formed From Coral Skeletal Carbonate by Hydrothermal Exchange," *Nature* 247 (1974) pp. 220–222. Two species of coral having a suitable pore size were identified for replicating into hydroxyapatite (HAp)and used as a bone substitute. Holmes. et al., "A Coralline Hydroxyapatite Bone Graft Substitute," *Clin. Orthop.* 188 (1984) pp. 252–262. To mimic the osteon evacuated stroma of cortical bone, the coral skeleton from the genus Porites was selected. To mimic the cancellous bone, the genus Goniopora was selected. Hanusiac, "Polymeric Replaminform Biomaterials and A New Membrane Structure," (Ph.D. thesis, Pennsylvania State University, 1977). However, porositys attained by natural corals, though reproducing that of tissues, appear questionable owing to the nature of the walls which contain impurities which are able to disturb the reaction mechanisms between ceramics and hard tissues. Osborn, "Hydroxylapatite Kermik granulate und ihro slatematik," *Zeitschrift Material* (1989) pp 2–12. In addition, Corralline HAp materials must still be formed into the desired macroscopic shape for implantation.

None of the current fabrication techniques enable the osteon-evacuated micro-architecture of the bone to be duplicated and none of these techniques allow the fabrication of a predetermined, tailored macro and micro-architecture.

Porous ceramics have been produced in many configurations and pore sizes using many processing routes. The most common approach for producing porous ceramic is via the replication of a polymeric porous structure. The process involves impregnation of a foam structure with ceramic materials by immersing it into a ceramic slip. The subsequent firing of the resultant structure pyrolyzes the substrate and sinters the ceramic powder. Porous HAp ceramics have been fabricated by Fabbri. et al. by impregnating cellulose sponge structures (interconnected macro-pores >150 microns) with HAp slurry. The main disadvantages of these replicas are there is no control of the architecture and the structures have inferior mechanical properties which limits their load bearing clinical applications.

Another approach to forming a porous ceramic is by incorporating volatile or combustible phase or phases that are lost during firing. This approach has been utilized for the fabrication of porous HAp ceramics using poly vinyl butyral as a porosifier, see Liu.

Another approach to forming ceramic porous structures is by the foaming of ceramic slurries. This involves incorporating a gaseous phase dispersed into a ceramic suspension. The suspension typically contains the ceramic material, water, a polymeric binder, a surfactant, and a gelling agent. Arita et al. obtained porous HAp ceramic sheets by means of a tape casting technique with $CaCO_3$ as a gas-forming agent. HAp ceramic sheets with a highly porous microstructure (up to 62%) were successfully developed. However, the pore size was limited to only several microns.

Solid free form fabrication (SFF) is a new manufacturing technology also known as rapid prototyping or layered manufacturing. Various SFF machines like stereolithography (SL), selective laser sintering (SLS), fused deposition modeling (FDM), laminated object manufacturing (LOM), and three-dimensional Printing (3d printing) are now commercially available. Recently, SFF has been used for medical prototyping. In medical applications, a physical model serves as a hard copy of the data set, illustrating the shape, orientation, relative location and size of internal anatomical structures for diagnosis, operation planning, design of implants, external and internal prostheses, surgical templates, and communication and teaching. See, McAloon, "Rapid Prototyping: A Unique Approach to Diagnosis and Planning of Medical Procedures," SME, Dearborn, Mich. (1997). The 3d printing process has been used for making polymeric medical devices. See Cima et al., "Fabrication of medical devices by solid free form fabrication," U.S. Pat. No. 5,490,962 (1996). Similarly SLS process has also been used for making bone prosthesis. See Fink. et al., "Rapid, Customized bone Prosthesis," U.S. Pat. No. 5,370,692 (1994).

The technique of stereolithography (SL) has been widely used for rapid prototyping of polymeric parts. See, Jacobs, "Rapid Prototyping and Manufacturing: Fundamentals of Stereolithography (Society of Manufacturing Engineers, Dearborn, Mich., 1993). The SFF method of SL has advantages over other SFF method in fabricating precision parts and high quality ceramic/polymer composite structures. The process of the current invention aims at fabricating end use structures for various applications rather than model prototypes by using biocompatible organics and inorganics in the SL process.

OBJECTS AND SUMMARY OF THE INVENTION

It is an object of this invention is to provide unique oxide ceramic and polymer/ceramic composites and unique non-oxide ceramic and polymer/ceramic composites having a porous network structure.

It is a further object of this invention to provide such ceramic composites with a macroshape, a network microarchitecture, a porosity and pore sizes in the network which can be simultaneously and precisely controlled or may be designed during the production process.

It is yet another object of this invention to provide a method for producing such composites.

It is still another object of this invention to produce such composites for use in various applications.

It is yet another object of this invention to provide a fabrication technique that enables the osteon-evacuated micro and macroarchitecture of the bone to be duplicated.

It is still another object of this invention to provide a fabrication technique that allows the production of predetermined micro-architectures.

It is still another object of this invention to provide such a composite structure that is made by an SLA fabrication technique using biocompatible materials.

All of the foregoing objects are achieved by the process of this invention which produces a ceramic or polymer/ceramic composite having a porous network. The process comprises providing a photocurable ceramic dispersion comprising a photocurable polymer and a ceramic composition, for making a photocurable dispersion. In this context, by the term "polymer" it is meant either a polymer molecule with functional groups that allow it to be reacted to form a connected three dimensional network during the laser curing, or a monomer solution which forms a connected three dimensional polymer network during the laser curing step. The polymer can either be bio-degradable or non-degradable. For bio-degradable polymers, the implant will be temporary and will be resorbed by the body over a period of time that can be tailored by the degradation rate of the polymer.

Preferably the ceramic structures of this invention are hydroxyapatite, beta tricalcium phosphate (TCP), calcium sulfate, and alumina ceramic structures. Other related ceramic phases, mixtures and solid solutions of predominantly calcium cations with phosphate, hydroxyl, sulfate, and hydrated water are also useful, as well as other compositions which would be known or obvious to those skilled in the art. The ceramic can be resorbable, such as beta tricalcium phospate, or nonresorbable, such as alumina. The dispersion is scanned with a laser to cure the photocurable polymer to produce a photocured composition.

Preferably and more specifically, the process uses a stereolithographic technique for laser patterning and photocuring a ceramic/polymer material. See Hull, U.S. Pat. No. 4,575,330, "Apparatus for production of three-dimensional objects by stereolithography," (1986) for details of the technique. The technique relies upon laser photocuring a dense colloidal dispersion into a desired complex three-dimensional shape. The shape may be obtained from a CT scan file of a bone and is rendered into a CAD file that is readable by the stereolithography instrument. The software is commercially available for translating the CT scan data to SL machine readable files. Additionally, the patient's defect site can be scanned to exactly match the implant or the device. See Crook, "Method for representing a patient's treatment site as data for use with a CAD CAM device," U.S. Pat. No. 5,452,407 (1995). Or the desired complex three-dimensional shape can be produced by conventional CAD (computer aided design) processes. The process can form a high quality orthopedic device that can also dimensionally match the bone structure of a patient. Stereolithography applied to bone implants has two potential advantages. The first is the rapid fabrication of individually shaped implants; and the second is fabrication of micro-porous materials that allow penetration of the cells into the graft and promotes new bone formation over time.

The ceramic composites having the described microarchitecture herein are fabricated or produced by Ceramic Stereolithography (CSL) that uses the SL machine for fabrication of three-dimensional shapes. More specifically, the CSL process of this invention is a solid freeform fabrication technique that fabricates a ceramic green body layer-by-layer from its CAD design by scanning an ultra-violet laser across the surface of a photocurable ceramic dispersion. If the desired object is a polymer/ceramic composite the object produced by the above mentioned stereolithographic process the object may be dried to remove volatile solvents, or may be post cured to complete the polymerization. These processes are well known to those skilled in the art of fabrication of purely polymeric objects via stereolithography (Jacobs. Paul F., "Fundamentals of Stereolithography," Soc. For Manufacturing Engineers, Dearborn, Mich., 1992). If the desired object is a purely ceramic material then the photocured composition is heated to a first temperature that is sufficient to burn out the photocured polymer. It is then heated to a second temperature that is higher than the first temperature and is sufficient to sinter the ceramic composition to produce a ceramic composite having a porous network. The sintering temperature can be controlled to fully density the ceramic or leave sub-micron pores in the structure.

The CSL fabrication process is used for producing a porous ceramic of controlled microarchitecture and pore size for use as a bone implant. The dispersion comprises ceramic powders dispersed with suitable dispersants in an aqueous or non-aqueous medium containing photo-curable polymers. For example, in bone grafting applications the micro architecture and pore sizes of the fabricated ceramic composite bone are obtained from an MRI or CAT scan file of osteon-evacuated bone. Optionally, the optimum bone architecture can be designed using CAD software. The shape of the fabricated bone graft structure, i.e. macro structure, may also be fabricated from the MRI scan of the real bone that is to be replaced.

The CSL fabrication process can replicate a virtual three-dimensional computer generated image into a real solid ceramic object. The ceramic structures have pore sizes ranging from sub-microns to 2000 microns and a porosity up to about 75%. The ceramic composites are useful, for example, in bone grafting, as orthopaedic implants, and for medical implant devices. Synthetic bone grafts are required for orthopedic uses such as bone graft substitute, augmentation, replacement, and fracture fixation materials, as well as in dental and head and neck uses such as craniofacial applications, and prosthetic implants. See Lemons, "Significance of the Porosity and Physical Chemistry of Calcium Phosphate Ceramics: Orthopedic Uses," *Annals of New York Academy of Sciences* 523, 278–82 (1988). Besides the medical application such composites can be used in structural applications or electronic applications.

BRIEF DESCRIPTION OF THE FIGURES

Other important objects and features of the invention will be apparent from the following Detailed Description of the Invention taken in connection with the accompanying drawings in which.

DETAILED DESCRIPTION OF THE INVENTION

Stereolithography (SL) is a sequential layering process. See, Jacobs, "Rapid Prototyping and Manufacturing-Fundamentals of Stereolithography," (SME, Dearborn, Mich. 1992). The CAD image of the object is sliced into thin sections and each section is then fabricated sequentially from the bottom up on a platform by scanning an ultraviolet laser on the surface of a photocurable polymeric fluid or photocurable polymer/ceramic particle dispersion. Henceforth the photocurable phase will be designated the "resin." The platform is sequentially lowered by one section thickness so that the resin covers the surface and the next section is patterned.

Figure 1:
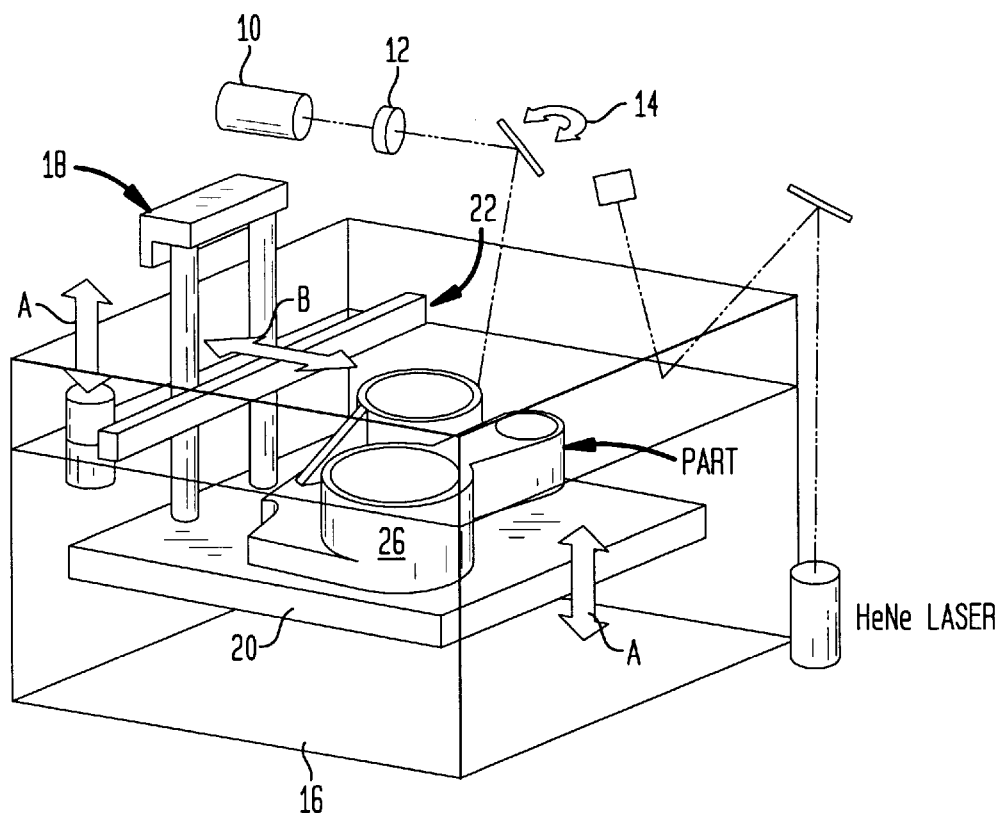
FIG. 1 is a schematic of the ceramic stereolithography process of this invention.

FIG. 1 is a schematic drawing of the SL process. An HeCd laser 10 is directed through lenses 12 onto mirror 14 which directs the beam onto a photocurable polymeric fluid or photocurable polymer/ceramic particle dispersion 16. An elevator 18 moves a platform 20 up and down in the direction of Arrows A. A sweeper 22 moves the platform 20 back and forth in the direction of Arrows B. A part 26 is formed layer by layer on the platform 20. The SL process requires computer software that allows a three dimensional CAD file of the object to be fabricated. The process further requires a laser photo curing material from which the part is to be fabricated. The combination of the tomography techniques for imaging bone structures (MRI and/or CAT scan) with stereo-lithography provides a unique way for the fabrication of bone replacement structures with the shape and pore size distribution of the in vivo scanned bone component. This invention is primarily directed to the fabrication of bone implants from biocompatible organics and inorganics by stereolithography which will duplicate the pore structure of a real bone and also allow for remineralization or which produce a controlled micro and macro structured device from biocompatible materials which can be used in orthopaedic applications. However, the methods and structures described herein have numerous other applications.

In fabrication of ceramics by SL, the resin is a concentrated (~10–60 volume % particles) colloidal ceramic dispersion in a photocurable polymeric fluid. A dispersant is normally added to aid in the dispersion of the ceramic particles. Additional photoinitiators or photosensitizers may be added as is well known in the art of purely polymeric SL. The polymeric fluid may comprise polymer chains with reactive functional groups which allow photocuring. Said polymers may be used alone (i.e. as a neat phase) if they are in a fluid state either at ambient conditions or at elevated temperatures if the SL process is conducted at elevated temperatures. Or the polymers may be dissolved in an appropriate aqueous or non-aqueous solvent. Or the continuous polymeric fluid phase may comprise a monomer or monomer/polymer mixture which polymerizes to produce a solid three dimensional polymer network upon photocuring. Useful polymer/monomers include ethylene glycol acrylates such as diacrylates, triacrylates, di and tri methacrylates and tetra acrylates. For basic oxide powders (i.e., those with high PH or isoelectric points) dispersants such as polymethacrylic acid work well. For acidic powders (i.e., with low isoelectric points) it is preferable to use cationic dispersants such as polyallyamine.

The cross-sectional shape of the solidified region resulting from scanning the laser are the building blocks for the SL process. The shape of the single cured line of the ceramic dispersion defines the resolution, the layer thickness, and laser scanning parameters in the SL process. The shape depends on the laser photon propagation in the concentrated colloidal dispersion. Photon propagation is determined by multiple scattering and absorption by particles and curing agents, respectively. By appropriately spacing apart the laser scanning pores that are less than 50 micron can be designed, which would otherwise be difficult to produce in the porous network. We have demonstrated, R. Garg. et al. "Optical Transmission in Highly-Concentrated Dispersions," *J. Opt. Soc. Am.* 15(4), 932–35 (1998), the entire disclosure of which is incorporated herein by reference, that the "Diffusion Model," Ishimaru, *"Wave Propagation and Scattering in Random Media,"* Vol. 1 (Academic Press, N.Y., 1978), p.175, describes the light propagation in colloidal dispersions. The diffusion model has been shown to accurately predict the line shape and penetration depth in concentrated photocurable ceramic dispersions. This quantitative model of light propagation in a ceramic dispersion is needed to predict curing depths; to calculate lateral light dispersion, which will cause broadening of cured lines; and to determine the spatial profile of photon intensity to program laser writing beam speeds required for curing.

The ceramic object thus fabricated from SL is subjected to conventional post processing drying, and thermal or UV curing steps. If a purely ceramic object is desired then the polymer phase is removed by polymer burnout. It is then sintered to completely densify the ceramic at elevated temperatures. The sintering temperature can be controlled to leave pores that are submicron to less than 10 micron in size. By use of the aforedescribed process, high quality monolithic ceramic objects of complex geometry have been produced.

EXAMPLES

An MRI scan of the bone image was taken from NIH Visible Human Project (Http://www.nlm.nih.gov/research/ visible/visible_human.html) and was converted into a three dimensional CAD image using "Materialize" computer software and then sliced into thin slices using "Maestro" (3D Systems, Inc.). Computer assisted tomography (CAT) and magnetic resonance imaging (MRI) scanning systems provide high resolution images of the internal structure of the human body. The Visible Human project from NIH provides a database of the MRI and CT scan of the entire human body. During the past few years, these scanning techniques, along with the associated software and hardware have undergone substantial development. It is now possible to represent the images into 3-D surface models or solid models. "Materialize" software converts the MRI or CT images into 3-D models.

Parts were then fabricated on 3D Systems SLA 250/40 stereolithography machine from a high concentration (48 volume%) aqueous alumina dispersion (0.5 μm alumina particles from Sumitomo Chemicals) using polyethylene glycol diacrylate (Sartomer) as a photocurable polymer and 2-Hydroxy-4-(2-hydroxyethoxy)-2-methylpropiophenone (Aldrich Chemicals) as the photoinitiator. The ceramic/organic composites thus fabricated were subjected to polymer burnout at 500 degree C., and then sintered at 1550 degree C. to a completely dense object.

Figure 2:
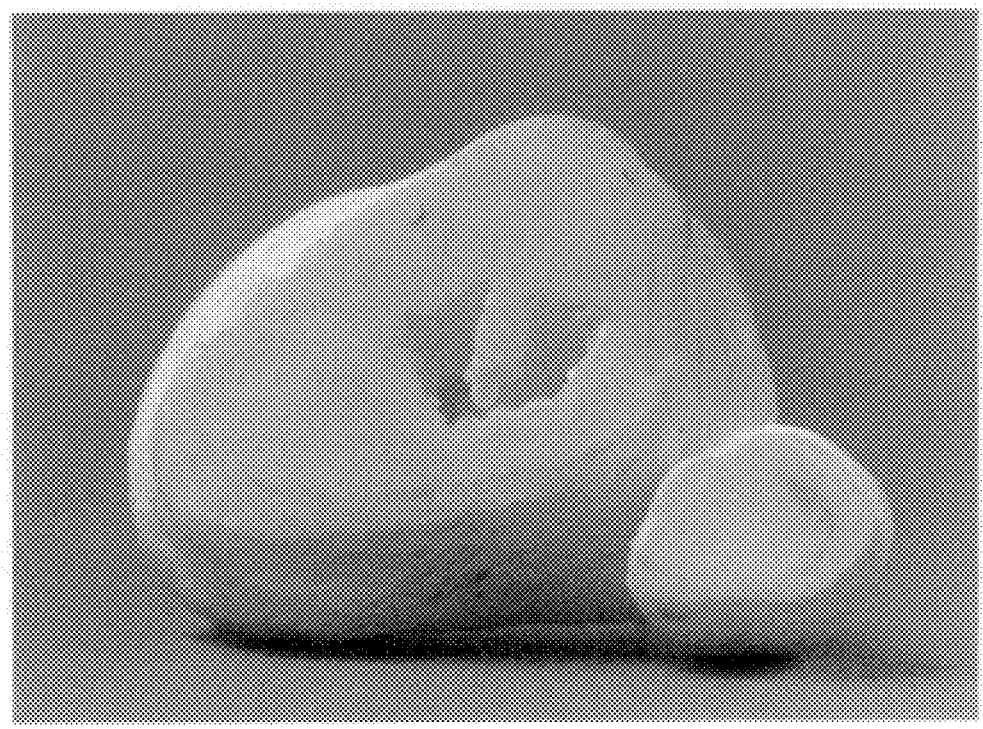
FIG. 2 is the bone structure fabricated from alumina dispersions by the stereolithography process of this invention.

FIG. 2 shows the section of a fabricated bone. The complex features of the bone are replicated faithfully. The resolution of the features in this case is limited by the resolution of the scanning software and the spot size of the laser beam. SL also allows fabrication of orthopedic implants with designed microstructure to allow for remineralization. An example of designed micro-architecture structure fabricated by the CSL technique is described next.

Figure 3:
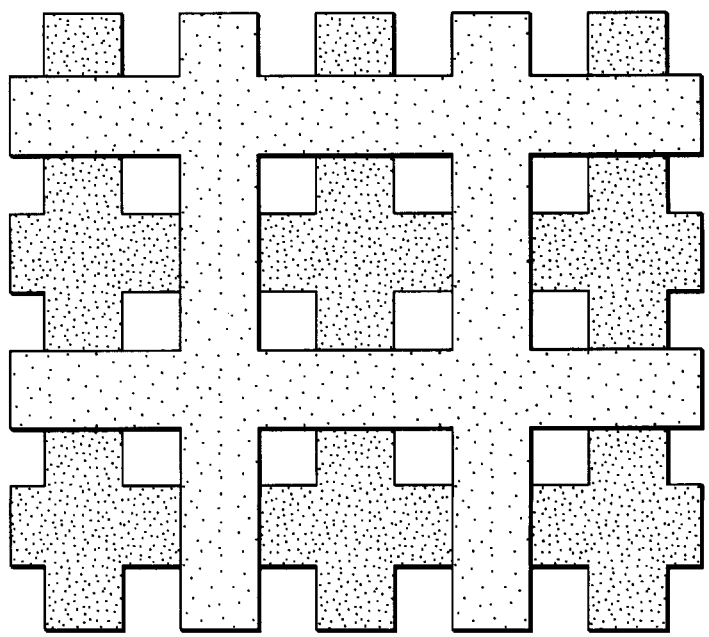
FIG. 3 is the bone implant of designed micro-architecture fabricated from hydroxyapatite by the stereolithography process of this invention.

FIG. 3 shows a bone graft of designed micro-architecture used for an implant. The design of the implant structure entailed individual layers of grids offset from each other to form two different pore sizes. This forms a continuous solid framework and a porous network of interconnected domains. The inter-connectivity of pores is very important for bone in-growth. For a given layer, a "macropore" is formed by the space between solid lines. After offsetting the layers, "micropores" are formed. Each layer is of same thickness as the "micropore" size, thereby limiting the three-dimensional interconnectivity to the "micropore" size. The final structure design was a cylinder of these offset grids, 8 mm in diameter and 2 mm in height. The implants with this structure, with interconnected pores of 150, 300 and 500 microns, and a constant porosity of 44.4%, were fabricated from high concentration alumina and hydroxyapatite dispersions in aqueous photocuring polymers. Pores may also be formed by not completely photocuring regions to create defects, and then converting the defects into pores by partial sintering.

More specifically, alumina and hydroxyapatite were used for producing the photocurable ceramic compositions for use in the CSL fabrication technique of this invention. Alumina was selected because it is chemically stable and is a widely used material for inert bioceramics used as surgical implants. The desired ceramic powders are of high purity and have particle sizes in the range of 0.05 microns to 10 microns and more preferably in the range of 0.1 to 5 microns. The preferred alumina powder used was a high purity (>99.99%) alpha-alumina from Sumitomo Chemicals with a mean particle size of 0.5 microns. Hydroxyapatite was used as a bone substitute because natural bone is approximately 70% hydroxyapatite by weight and 50% hydroxyapatite by volume. Hydroxyapatite has also been widely used for various implant applications such as bioactive space fillers, as scaffolding for the in-growth of tissues, and as a coating for implants to promote bonding with tissue.

The preferred ceramic dispersions were made by adding the alumina powder to water using 1 weight % of a 15,000 Mw ammonium salt of polymethacrylic sold (R. T. Vanderbilt Company, Inc.) as the dispersant. The dispersions were then ultrasonicated for five minutes to homogenize and break the soft agglomerates. The composition was then de-aired under vacuum for five minutes and then the photocuring polymers were added. A preferred polymer is a UV curable polymer, polyethylene glycol diacrylate (Sartomer, Inc.). The final photocurable ceramic dispersion contains 48 volume % alumina and 7 volume % polymer. A hydroxyapatite dispersion from CAM Implants, Netherlands, as supplied, was used to make a similar photocurable ceramic dispersion. The UV curable polymer, polyethylene glycol diacrylate (Sartomer, Inc.) was added to the hydroxyapatite dispersion resulting in a final dispersion containing 21 volume % HAp.

In both cases the photocurable ceramic dispersion had viscosities low enough to be processed by conventional SL procedures. Viscosities between 10 Pa-s and 1 mPa-s are desirable for SL processes, and more preferably viscosities between 0.3 Pa-s and 5 mPa-s.

Two different designs were selected for the fabrication of the bone implants. The first was a micro-architecture of the bone designed using AutoCAD™.

FIG. 3 depicts the fabricated article from the first design. The solid framework and the porous network are continuous and have interconnected domains. This design for a fabricated article was chosen to demonstrate the ability to fabricate a predetermined, i.e., tailor made, micro-architecture and pore size. The porosity and the pore size can be precisely controlled by changing the thickness of the solid section and the thickness of the porous section in the design file.

For the second fabricated article, an MRI scan of a leg-bone was taken from the NIH Visible Human Project and was converted into a three dimensional CAD image using the "Materialize" computer software application. The resolution of the MRI scan was limited to 1 mm and thus it does not capture the porous, micro-architecture of the bone. This design was selected to demonstrate the feasibility of fabricating complex bone structure for custom implant applications.

The stereolithography machine (SLA 250/40 3D Systems, Inc.) used herein had a He-Cd laser operating at wavelength of 325 mm and beam diameter (2Wo) of 250 μm. The CAD design file was sectioned into thin slices of 100 um layer thickness using "Maestro" software to render into a machine readable file. The experimentally obtained penetration depth (Dp) and critical exposure (Ec) values were used in the fabrication and the hatch spacing and the recoater parameters were adjusted according to the cured profile. To precisely control the micro-architecture, precise understanding of Dp and Ec and curing profile was required. More specifically, Dp value of 75 microns and Ec value of 30 mJ/cm$^2$ was used along with hatch spacing of 75 microns.

The green body fabricated was thoroughly washed with distilled water and dried overnight in vacuum at 60° C. The green body was then was subjected to polymer burnout at 500° C. Subsequently, the alumina parts were sintered at 1500° C. and HAp parts were sintered at 1150° C. The resulting density of the structures was greater than 99% of the theoretical density for the alumina structures and greater than 95% of the theoretical density for the hydroxyapaptite structures. By controlling the sintering rates and sintering temperature the micropores can be created in the object.

FIG. 2 shows an implant of this invention with a designed microstructure that was fabricated by the process of this invention. Three different pore size structures of the design were fabricated from alumina and from hydroxyapatite. The pore sizes were 150 μm, 300 μm and 500 μm. A constant porosity of 44.4% was maintained for each pore size. The porosity can be easily varied by changing the thickness of the solid section.

For the 150 μm structure, the solid component of the implant framework was 300 μm and the macro-pores were 600 μm interconnections are 150 μm with 3—3 connectivity. For the 300 μm structure, macro-pores were 1200 μm with inter-connectivity of 300 μm and 500 μm structures have macro-pores of 2000 μm. The fabricated micro-architecture and size was precisely as designed in the CAD file.

The bone structure fabricated from the MRI image was ⅕ the size of the original file. Two different sections were fabricated, one near the knee and other on the femur.

FIG. 2 shows the section of the fabricated bone. It can be seen that the complex features of the bone are replicated faithfully.

A alumina dispersion was also made by dispersing the alumina powders in a pure photocurable monomer phase. More specifically, a commercial epoxy resin (SL5170, 3D Systems) was used as the photocurable monomer. The dispersion was made by adding alumina powder to the resin using PMAA as the dispersant. The final dispersion contained 29 volume % alumina and 0.3 weight % PMAA. An object in the shape of "P" was made using this photcurable alumina dispersion by the process of this invention.

The foregoing demonstrates that the processes of this invention are capable of fabricating bone replacement structures using stereolithography techniques. The SL technique allows for fabricating orthopæedic implants with controlled pore sizes and porosity as well as with controlled macroscopic shape. The macroshape of the implant structure can be precisely controlled to fit the patient and can be designed from the in vivo scan of the bone. The processes of this invention provides a unique way for fabricating custom implants. It further demonstrated that predesigned ceramic composite structures can be precisely fabricated by the process of this invention that will be useful in various applications, such as ceramic prototyping.

While several advantageous embodiments have been chosen to illustrate the invention, it will be understood by those skilled in the art that various changes and modifications can be made therein without departing from the scope of the invention as defined in the appended claims.

What is claimed is:

1. A process for producing a ceramic composite bone implant having a porous network comprising:
   providing a photocurable ceramic dispersion comprising a photocurable polymer and a high volume percent ceramic composition of alumina, silica, zirconia, barium titanate or silicon nitrite or mixtures thereof, the dispersion having an free fluid surface;
   scanning the free fluid surface of the photocurable ceramic dispersion in a grid pattern with a laser to cure the photocurable polymer to produce a layer of photocured composition having a grid pattern;
   scanning the free fluid surface of the photocurable ceramic dispersion in a grid pattern with a laser to cure the photocurable polymer to produce a second layer of photocured composition having a grid pattern, the grid patterns of the first and second layers being offset to form a porous network;
   continuing to scan the free fluid surface of the photocurable ceramic dispersion in a grid pattern with a laser to cure subsequent layers of the photocurable polymer to produce subsequent layers of photocured composition with offset grid patterns;
   removing uncured polymer and dispersion from the composition; and
   drying or post-polymerization using UV or thermally curing the composition to produce a porous composite bone implant material which is suitable as a bone implant material or a device for orthopaedic implantation.

2. The process of claim 1 further comprising heating the photocured composition to a first temperature that is sufficient to burnout the photocured polymer, and then heating the composition to a second temperature that is higher than the first temperature and is sufficient to sinter the ceramic composition.

3. The process of claim 2 further comprising MRI scanning a bone to be duplicated to produce MRI data and converting the MRI data into three dimensional CAD image data and scanning the laser using the CAD image data.

4. The process of claim 1 wherein the photocurable polymer is biodegradable.

5. The process of claim 3 wherein the bone implant has pore sizes ranging from about 0.5 microns to 2000 microns and a porosity up to 75 percent.

6. A process for producing a ceramic composite bone implant having a porous network comprising:
   providing a photocurable ceramic dispersion comprising a photocurable polymer and a high volume percent ceramic composition of alumina, silica, zirconia, barium titanate or silicon nitrite or mixtures thereof, the dispersion having an free fluid surface;
   scanning the free fluid surface of the photocurable ceramic dispersion with a laser to cure the photocurable polymer to produce a photocured composition;
   removing uncured polymer and dispersion from the composition;
   incompletely drying or post-polymerization using UV or thermally curing the composition to produce a composite bone implant material which is suitable as a bone implant material or a device for orthopaedic implantation, the composite bone implant material having defects resulting from incompletely drying or curing the composition; and
   partially sintering the composite bone implant material to form the defects into pores.

7. The process of claim 6 further comprising heating the photocured composition to a first temperature that is sufficient to burnout the photocured polymer, and then heating the composition to a second temperature that is higher than the first temperature and is sufficient to sinter the ceramic composition.

8. The process of claim 7 further comprising MRI scanning a bone to be duplicated to produce MRI data and converting the MRI data into three dimensional CAD image data and scanning the laser using the CAD image data.

9. The process of claim 6 wherein the photocurable polymer is biodegradable.

10. The process of claim 8 wherein the bone implant has pore sizes ranging from about 0.5 microns to 2000 microns and a porosity up to 75 percent.

11. A process for producing a ceramic composite bone implant having a porous network comprising:
   providing a photocurable ceramic dispersion comprising a photocurable polymer and a high volume percent ceramic composition of hydroxyapatite or beta TCP or mixtures thereof, the dispersion having an free fluid surface;

scanning the free fluid surface of the photocurable ceramic dispersion in a grid pattern with a laser to cure the photocurable polymer to produce a layer of photocured composition having a grid pattern;

scanning the free fluid surface of the photocurable ceramic dispersion in a grid pattern with a laser to cure the photocurable polymer to produce a second layer of photocured composition having a grid pattern, the grid patterns of the first and second layers being offset to form a porous network;

continuing to scan the free third surface of the photocurable ceramic dispersion in a grid pattern with a laser to cure subsequent layers of the photocurable polymer to produce subsequent layers of photocured composition with offset grid patterns;

removing uncured polymer and dispersion from the composition; and drying or post-polymerization using UV or thermally curing the composition to produce a porous composite bone implant material which is suitable as a bone implant material or a device for orthopaedic implantation.

12. The process of claim 11 further comprising heating the photocured composition to a first temperature that is sufficient to burnout the photocured polymer, and then heating the composition to a second temperature that is higher than the first temperature and is sufficient to sinter the ceramic composition.

13. The process of claim 12 further comprising MRI scanning a bone to be duplicated to produce MRI data and converting the MRI data into three dimensional CAD image data and scanning the laser using the CAD image data.

14. The process of claim 11 wherein the photocurable polymer is biodegradable.

15. The process of claim 13 wherein the bone implant has pore sizes ranging from about 0.5 microns to 2000 microns and a porosity up to 75 percent.

16. A process for producing a ceramic composite bone implant having a porous network comprising:

providing a photocurable ceramic dispersion comprising a photocurable polymer and a high volume percent ceramic composition of hydroxyapatite or beta TCP or mixtures thereof, the dispersion having an free fluid surface;

scanning the free fluid surface of the photocurable ceramic dispersion with a laser to cure the photocurable polymer to produce a photocured composition;

removing uncured polymer and dispersion from the composition; and incompletely drying or post-polymerization using UV or thermally curing the composition to produce a composite bone implant material which is suitable as a bone implant material or a device for orthopaedic implantation, the composite bone implant material having defects resulting from incompletely drying or curing the composition; and partially sintering the composite bone implant material to form the defects into pores.

17. The process of claim 16 further comprising heating the photocured composition to a first temperature that is sufficient to burnout the photocured polymer, and then heating the composition to a second temperature that is higher than the first temperature and is sufficient to sinter the ceramic composition.

18. The process of claim 17 further comprising MRI scanning a bone to be duplicated to produce MRI data and converting the MRI data into three dimensional CAD image data and scanning the laser using the CAD image data.

19. The process of claim 16 wherein the photocurable polymer is biodegradable.

20. The process of claim 18 wherein the bone implant has pore sizes ranging from about 0.5 microns to 2000 microns and a porosity up to 75 percent.

* * * * *